United States Patent [19]
Kovac et al.

[11] Patent Number: 5,921,979
[45] Date of Patent: Jul. 13, 1999

[54] APPARATUS AND METHOD FOR TISSUE AND ORGAN STABILIZATION

[75] Inventors: Tim J. Kovac, Los Gatos; Peter S. Brown, Mountain View; Albert K. Chin, Palo Alto, all of Calif.

[73] Assignee: Guidant Corporation, Indianapolis, Ind.

[21] Appl. No.: 08/774,855

[22] Filed: Dec. 18, 1996

[51] Int. Cl.⁶ .................................................. A61B 17/00
[52] U.S. Cl. ................................................................ 606/1
[58] Field of Search .................................. 606/213–216; 600/195, 201, 210, 217, 235, 391; 607/127; 604/180, 174

[56] References Cited

U.S. PATENT DOCUMENTS

| | | | |
|---|---|---|---|
| 4,051,842 | 10/1977 | Hazel et al. | 600/391 |
| 5,148,806 | 9/1992 | Fukui et al. | 600/391 |
| 5,415,666 | 5/1995 | Gourlay et al. | . |
| 5,425,705 | 6/1995 | Evard et al. | . |
| 5,733,305 | 3/1998 | Fleischmann | 606/215 |

OTHER PUBLICATIONS

Goldstein, Harold S. M.C., FACS, *A Novel Technique for Anterior Hernia Repair*, Reprint RE–2028–Rev. A (Undated).

*Primary Examiner*—Michael Buiz
*Assistant Examiner*—William W. Lewis
*Attorney, Agent, or Firm*—Fulwider Patton Lee & Utecht, LLP

[57] ABSTRACT

A system for locally stabilizing an anastomotic site of a vessel of a beating heart during a surgical procedure is disclosed. The system includes bonding a pad to the myocardium and attaching a control arm to the pad, all by use of a bioabsorbable adhesive. The control arm is grasped and manipulated by a retractor thereby stabilizing the anastomotic area during the surgical procedure. The pad is optional and can be ommitted in one embodiment where the control arm has feet that are directly bonded to tissue. The pad may also have barbs or can include suction cups. The pad can include a helix-shaped fastener or a mechanical fastener that can be easily linked or hooked to a surgical instrument for manipulation.

57 Claims, 3 Drawing Sheets

APPARATUS AND METHOD FOR TISSUE AND ORGAN STABILIZATION

BACKGROUND OF THE INVENTION

The present invention relates to an apparatus and method for stabilizing an area of tissue during a surgical procedure. More precisely, the present invention is directed to an apparatus and method to manipulate and locally stabilize an anastomotic site during a beating heart coronary artery bypass grafting procedure.

Various cardiovascular procedures have been performed for many years typically by opening the sternum (referred to as a median sternotomy), and connecting the patient to cardiopulmonary bypass equipment to maintain the circulation of oxygenated blood throughout the patient's circulatory system. In this manner, the heart can be stopped and various surgical procedures performed such as coronary artery bypass grafting and replacement of aortic, mitro, and other heart valves. Numerous other surgical procedures have been performed in a similar manner.

During minimally invasive coronary artery bypass procedures using the beating heart approach, the region of the heart which receives the graft vessel must be stabilized. Presently, this is often performed by threading two suture or silicone rubber strands through the myocardium with curved needles, on either side of the recipient coronary artery at the site of the distal anastomosis. The silicone strands are tensioned to lift the heart and to hold the coronary artery stationary. Suture or silicone strands with curved needles swaged on one end are available for this use.

Placement of the suture or silicone loops may be somewhat difficult, as the heart is beating. The tip of the needle must be placed on the heart, and rotation of the surgeon's wrists must be performed to insert the needle through the myocardium. Unpredictable motion of the epicardial surface during needle placement may cause laceration of the heart or puncture of a coronary artery. It is therefore useful to stabilize the anastomotic area during the surgical procedure.

There are devices and methods that facilitate the performance of cardiac procedures such as heart valve repair and replacement, coronary artery bypass grafting, and the like, using minimally invasive techniques to eliminate the need for a gross thoracotomy. For example, U.S. Pat. No. 5,425,705 to Evard et al. discloses an apparatus and method for thoracoscopically arresting the heart and establishing cardiopulmonary bypass, thus facilitating a variety of less-invasive surgical procedures on and within the heart and great vessels of the thorax. In one embodiment, Evard provides a thoracoscopic system for arresting a patient's heart including a clamp configured for introduction into the patient's thoracic cavity through a percutaneous intercostal penetration in the patient's chest. The clamp is positionable about the patient's ascending aorta between the coronary arteries and the brachiocephalic artery. The clamp is coupled to the distal end of an elongated handle for manipulating the clamp from a location outside of the patient's thoracic cavity. It is known to use surgical clips or clamps for the purpose of clamping vessels or manipulating tissue. Typically, such clamps have a pair of movable jaws biased by a spring into a closed position, allowing the clamp to be placed on a vessel or portion of tissue and be firmly retained thereon. Examples of such clamps can be found in U.S. Pat. No. 4,932,955 to Merz et al.; U.S. Pat. No. 4,605,990 to Wilder et al.; U.S. Pat. No. 5,074,870 to Von Zeppelin; U.S. Pat. No. 3,809,094 to Cook; U.S. Pat. No. 4,404,677 to Springer; U.S. Pat. No. 4,051,844 to Chiulli; and U.S. Pat. No. 4,988,355 to Leveen et al.

Outside of the field of cardiac surgery, U.S. Pat. No. 5,415,666 to Gourlay et al. discloses a tethered clamp retractor used for tissue manipulation. The tissue manipulation system includes a tethered clamp, a clamp applicator for positioning the clamp through a trocar sleeve and applying the clamp to a tissue location in the abdominal cavity, and a rigid positioning shaft for engaging the clamp and/or tether to manipulate the clamp.

In view of the shortcomings of the prior art devices, there is a specific need for an apparatus and method for locally stabilizing an anastomotic site during a beating heart coronary artery grafting procedure.

SUMMARY OF THE INVENTION

The present invention is directed to a system and method for locally stabilizing an anastomotic site of a beating heart during a cardiac surgical procedure. In a preferred embodiment, the present invention system includes a pad of bioabsorbable adhesive attached to an area of cardiac tissue, means for controlling the pad and thereby manipulating the area of cardiac tissue to create a locally stable area, and means for bonding the pad to the area of tissue. A retractor is used to grasp the means for controlling the pad, which means may be a rigid control arm. In a preferred method of the present invention, the procedure comprises exposing and drying off the anastomotic area of the heart's surface, placing a structural component or pad in the form of a bioabsorbable glue to tissue adjacent the coronary artery, letting the glue cure, attaching a retractor to the structural component or pad, and manipulating the structural component to minimize movement and stabilize the anastomotic site surrounding the artery.

In an alternative embodiment, the present invention provides a system for locally stabilizing the myocardium adjacent to an anastomotic site of a coronary artery of a beating heart during a surgical procedure, the system having a first helix-shaped fastener inserted into the myocardium adjacent the coronary artery, a second helix-shaped fastener inserted into the myocardium adjacent the coronary artery, and at least one suture attached to each of the first and second helix fasteners whereby the sutures are tensioned to stabilize the myocardium and the coronary artery.

In the exemplary embodiment, the present invention employs a strand of suture attached to the helix-shaped fastener. The helix-shaped fastener is inserted into the myocardium adjacent the anastomotic site of the coronary artery by means of a mechanical insertion device. A second helix-shaped fastener is inserted on the opposite side of the artery and tension is applied to suspend and stabilize the anastomotic site. Because the helix-shaped fastener involves placement of the tip of the device on the heart and depression of the insertion device handle, it is faster and simpler than use of the conventional curved needle insertion. The helix-shaped fastener advances axially, similar to that of a corkscrew, into the myocardium, and the rotational maneuver of a conventional needle placement is avoided. In the preferred embodiment, the helix-shaped fastener is manufactured form a rigid, bioabsorbable material. Rigidity of the fastener is required to allow insertion into the myocardium; use of a bioabsorbable material allows the fastener to be left in the heart tissue following coronary bypass without need for its removal. The suture attached to the fastener may also be bioabsorbable, such that following use, the suture may be cut close to the fastener and the remaining short end left behind as well.

The sutures may be attached to a frame outside the surface of the skin of the patient; the frame may encircle the limited thoracotomy, or sternotomy used for cardiac access. Alternatively, the sutures may be attached to a frame which in turn is attached to the operating table. It is anticipated that two helix-shaped fasteners be used on opposite sides of a coronary artery for stabilization, although additional helix-shaped fasteners may be added as needed.

These and other advantages of the present invention will become apparent from the following detailed description thereof when taken in conjunction with the accompanying exemplary drawings.

DETAILED DESCRIPTION OF THE PREFERRED EMBODIMENTS

The present invention is directed to a system and method for locally stabilizing an anastomotic site of a beating heart during a cardiac surgical procedure. While the present invention is described in detail as applied to minimally invasive coronary artery bypass graft procedures on a beating heart, those skilled in the art will appreciate that the present invention can be applied to other surgical procedures and internal organs as well where locally stabilizing tissue is a primary concern.

Figure 1:
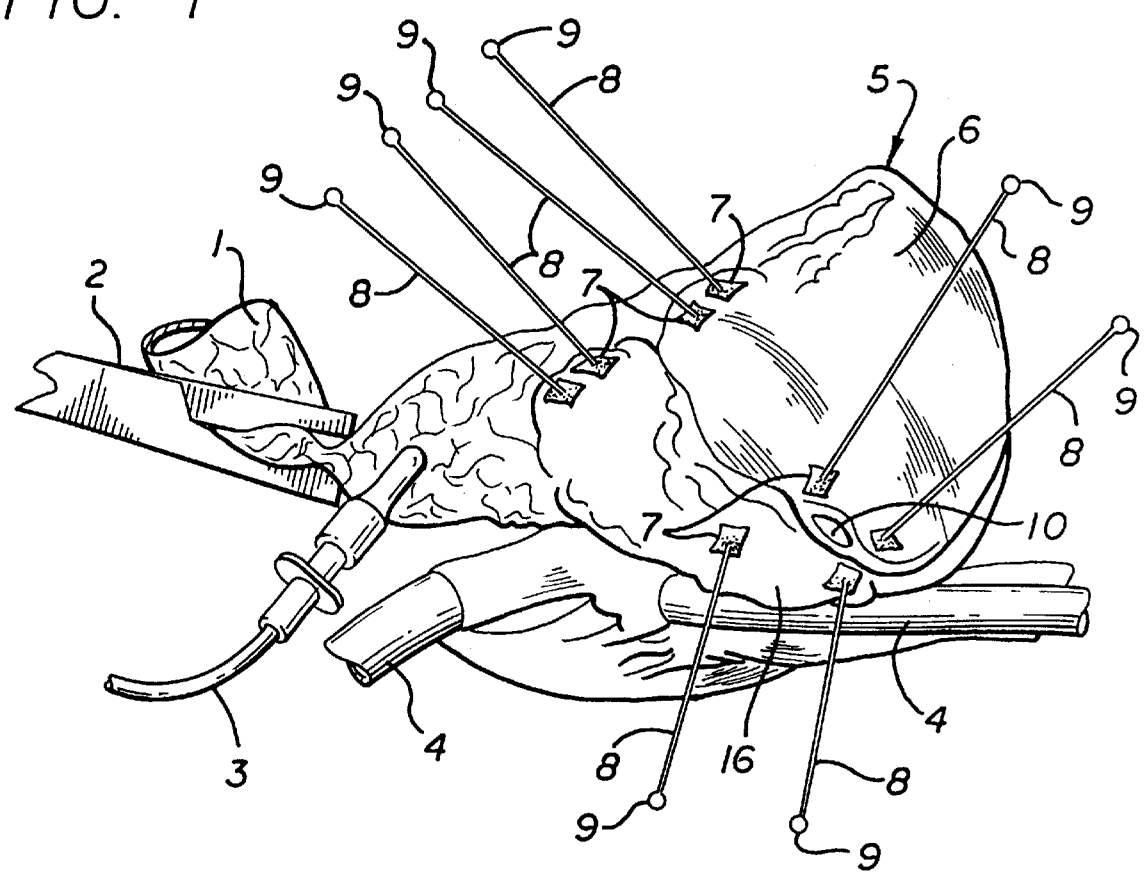
FIG. 1 is a perspective view of a preferred embodiment of the present invention in use to locally stabilize an anastomotic site during a coronary artery bypass grafting procedure.

FIG. 1 is a perspective view of a conventional cardiopulmonary bypass procedure. As taught by conventional techniques, cardiopulmonary bypass is established by a venous cannula that is introduced into a major vein such as the inferior vena cava, or into the heart 5 itself, to withdraw deoxygenated blood from the patient and route it to a cardiopulmonary bypass (CPB) machine for oxygenation. Generally, an arterial cannula is introduced into a major artery such as the aorta, or a femoral artery, to deliver oxygenated blood from the cardiopulmonary bypass machine to the patient's arterial system.

In surgical procedures where cardiac function is arrested, the heart and coronary arteries must be isolated from the patient's arterial system. Using conventional techniques, the sternum is cut longitudinally, referred to as a median sternotomy, to provide access to the heart and other thoracic vessels. One method taught in the prior art is to mechanically cross-clamp the ascending aorta 1 with a clamp 2 downstream of the ostia of the coronary arteries, but upstream of the brachiocephalic artery, which allows oxygenated blood from the cardiopulmonary bypass machine to reach the arms, neck, head, and the remainder of the body. A catheter 3 can then be introduced into the ascending aorta 1 between the cross-clamp 2 and the aortic valve. Cardioplegic fluid is then infused through the catheter 3 and into the coronary arteries. The venous cannula 4 introduced into the heart 5 withdraws deoxygenated blood from the patient and routes it to the cardiopulmonary bypass machine for oxygenation.

The pericardium in FIG. 1 has been omitted for clarity. FIG. 1 further shows a preferred embodiment of the present invention attached to myocardium 6. In this embodiment, pads 7 are attached to the myocardium 6 adjacent to and on either side of coronary artery 10. The pads 7 can be formed from a bioabsorbable adhesive that attaches directly to the myocardium, as will be further described herein. While pads 7 in FIG. 1 are depicted as a rectangular-shaped patch on the myocardium, in practice it is more likely to resemble a highly viscous and flowable adhesive that will flow onto the myocardium and provide a surface that can be manipulated. In keeping with the invention, a surgical instrument, such as a known grasper or retractor (not shown) is used to grasp and manipulate pads 7 and hence the myocardium, to lift and stabilize the tissue of the anastomotic area 16 surrounding coronary artery 10. To facilitate manipulation of pads 7, control arms 8 are attached to the pads. The control arms can either be flexible bioabsorbable material, such as suture thread adhesively attached to the pads, or a more rigid material attached to the pads. The retractor or grasper is used to removably grip control arms 8 and pull and lift the tissue to stabilize the area 16 around coronary artery 10 as described.

Figure 2:
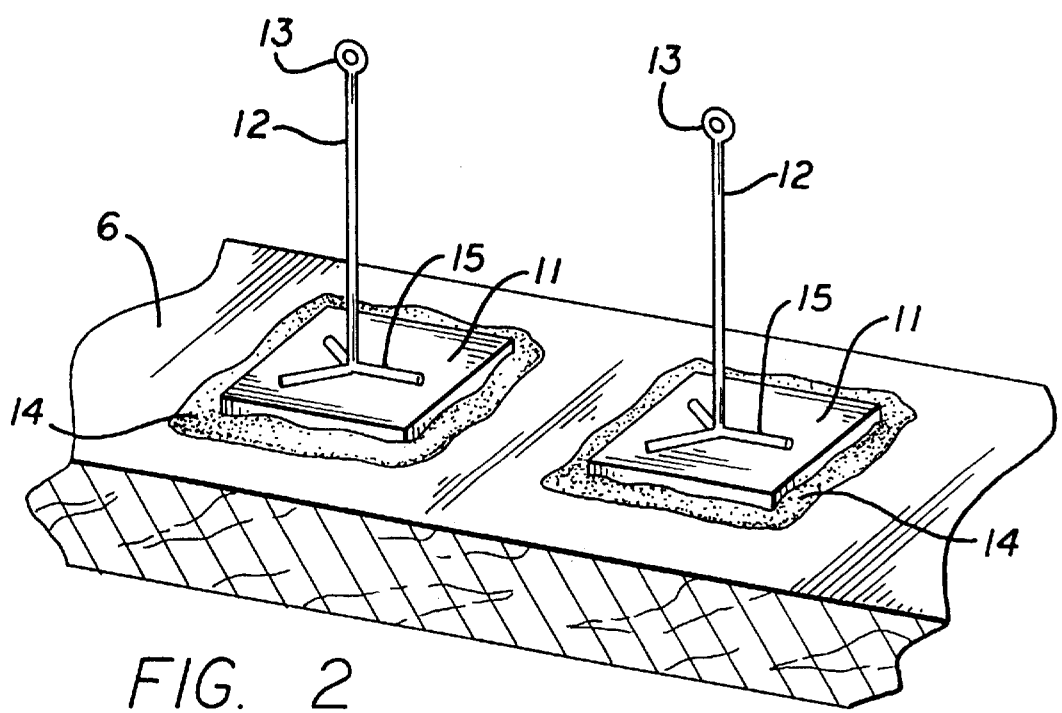
FIG. 2 is a perspective view of a preferred embodiment of the present invention attached to the myocardium.

In another preferred embodiment, as shown in FIGS. 1 and 2, the present invention provides pads 7 adhesively bonded to myocardium 6. Further, control arm 8 is attached to each of the respective pads 7. These control arms 8 have an attachment member 9 that permit a surgical instrument, such as a retractor (not shown), to manipulate control arm 8 when gripping attachment member 9. Accordingly, when the retractor controls the movement of control arm 8, pad 7 and the cardiac tissue directly beneath are stabilized so that anastomotic site 16 is likewise stabilized for the subsequent grafting procedure.

Although FIG. 1 shows a surgical procedure wherein the cardiac function is arrested using cardiopulmonary bypass procedures, the present invention has even greater value in a beating heart wherein anastomotic site 16 must be stabilized for the grafting process.

FIGS. 2–9 are perspective and side elevational views of various alternative embodiments of the present invention system. FIG. 2 provides a perspective view of the present invention system comprising pad 11, control arm 12 connected to pad 11 wherein control arm 12 terminates in attachment member 13. Attachment member 13 in this embodiment is a ring that facilitates easy grasping by a surgical instrument such as a grasper, a retractor or the like. Control arm 12 is attached to pad 11 by use of adhesive 14, preferably the same adhesive used to bond pad 11 to myocardium 6. Pad 11 appears in FIGS. 1 and 2 as small rectangles, but other shapes and sizes are contemplated depending upon surgical constraints. In addition, pad 11 is preferably made from a pliable material so that it easily conforms to match the surface contours of myocardium 6.

Control arm 12 is made from a rigid or semirigid material and further includes optional feet 15 that spread outward to obtain torsional and bending control of pad 11. This control arm, pad, and retractor system allows six degrees of control of the structural pieces in the X, Y, and Z axes along with moments about each of those axes.

Feet 15 can have any number of outstretched toes dispersed in a variety of angles and configurations. Control arm 12 preferably has a cylindrical shape, or it can have a polygonal shape cross-section.

In one exemplary embodiment, pad 11, control arm 12, and adhesive 14 are made from bioabsorbable materials. After the surgical operation, control arm 12 can be cut and removed while feet 15, pad 11, and adhesive 14 are left behind to dissolve within the patient. In an exemplary embodiment, adhesive 14 is made from is a bioabsorbable copolymer such as, for example, poly-L-lactic acid (L-PLA), polycaprolactone (PCL), collagen based adhesive, albumin based adhesive, and fibrin based adhesive. Pad 11 and control arm 12 are preferably made from bioabsorbable materials such as, for example, polyglycolic acid (PGA), poly-L-lactic acid (L-PLA), polyorthoesters, polyanhydrides, polyiminocarbonates, inorganic calcium phosphate, polyorthoesters, aliphatic polycarbonates, and polyphosphazenes.

Figure 3:
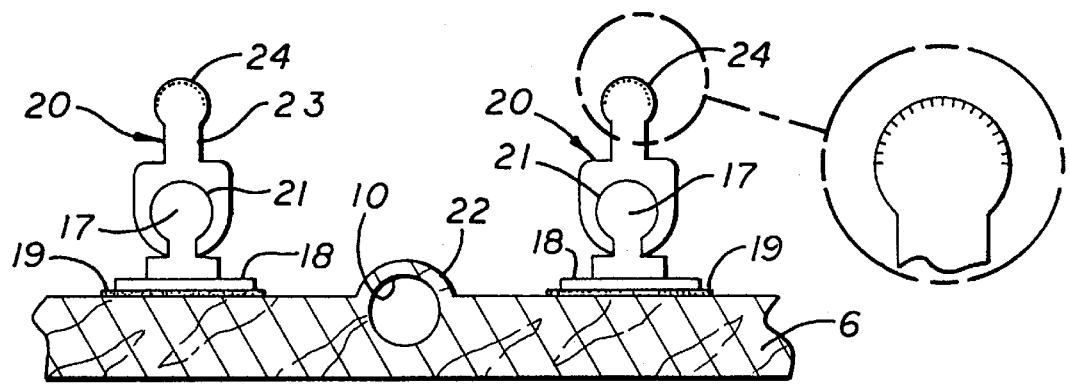
FIG. 3 is a side elevational view of an alternative embodiment of the present invention using mechanically linked fasteners.

FIG. 3 provides a side elevational view of an alternative embodiment of the present invention system attached to myocardium 6 adjacent vessel or artery 16. In this embodiment, the system includes mechanical interlock 17 bonded by optional pad 18 to myocardium 6 by use of adhesive 19. Traction frame 20 having interior opening 21 that mechanically locks with the complementary shape of interlock 17 thereby interconnecting the two structures. Specifically, interlock 17 can have a ball or cylindrical shape while opening 21 can have a complementary tubular cavity to link up therewith. Sliding the traction frame 20 laterally would connect and disconnect opening 21 to and from interlock 17.

Traction frame 20 includes control arm 23 that terminates in an enlarged, grippable structure such as textured end 24 as shown. Textured end 24 is grasped by a retractor to manipulate the tissue connected to pad 18. Thus, through the present invention system, it is possible to lift and pull myocardium 6 thereby locally stabilizing anastomotic site 22. If interlock 17, pad 18, and adhesive 19 are made from bioabsorbable materials, they can be left behind after the procedure to dissolve within the patient after traction frame 20 is disconnected therefrom.

Figure 4:
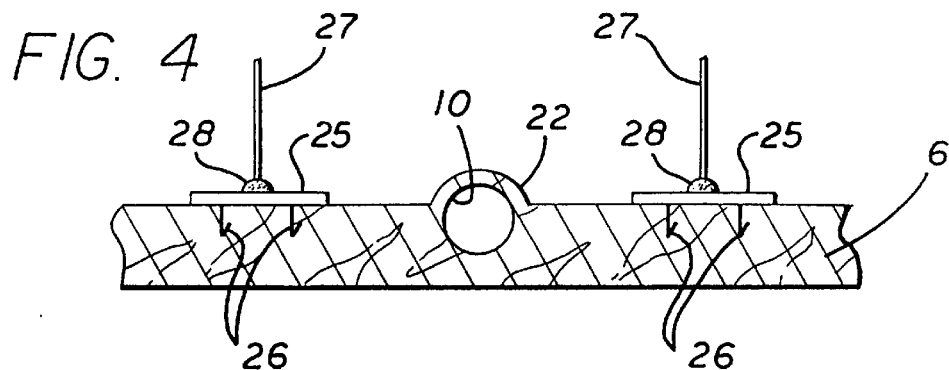
FIG. 4 is a side elevational view of an alternative embodiment of the present invention having a pad with barbs that are embedded in the myocardium.

FIG. 4 provides a side elevational view of an alternative embodiment where pad 25 has at least one barb 26 embedded into myocardium 6. The barb(s) 26 assist in attaching pad 25 to myocardium 6. Each pad 25 includes suture 27 bonded to pad 25 by use of adhesive 28. Of course, sutures 27 can be replaced with rigid or semirigid control arms in an alternative embodiment. The sutures 27, are in turn, connected to an optional frame (not shown) that is positioned outside the patient encircling the limited thoracotomy or sternotomy used for cardiac access. Alternatively, sutures may be attached to a frame that is in turn attached to the operating table.

Figure 5:
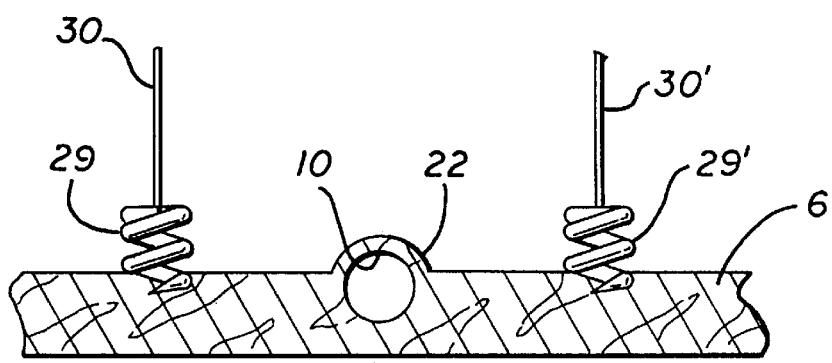
FIG. 5 is a side elevational view of an alternative embodiment of the present invention wherein helix-shaped fasteners are used to locally stabilize the anastomotic site.
Figure 6A:
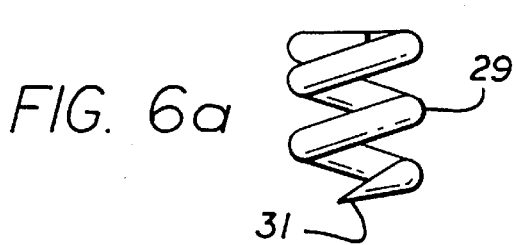
FIGS. 6 (a) and (b) are a side elevational view and a top plan view, respectively, of a preferred embodiment of the present invention helix-shaped fastener.
Figure 6B:
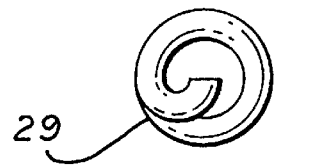

FIG. 5 provides a side elevational view of an alternative embodiment system providing preferably helix-shaped fasteners 29 for embedding into myocardium 6 on either side of artery 10. FIGS. 6(a) and 6(b) provide a side elevational view and a top plan view, respectively, of a preferred embodiment of the helix-shaped fastener 29. As seen in FIG. 5, the helix-shaped fastener 29 is ideally inserted into myocardium 6 adjacent anastomotic site 22 of coronary artery 10 by means of a mechanical insertion device or manually.

A second helix-shaped fastener 29' and associated suture 30' are inserted on the opposite side of artery 10 and tension is applied to suspend and stabilize anastomotic site 22 by use of sutures 30, 30' attached to fasteners 29, 29'. In the preferred embodiment, helix-shaped fasteners 29, 29' are manufactured from a rigid, bioabsorbable material. Rigidity of fasteners 29, 29' is required to allow insertion into myocardium 6; use of a bioabsorbable material allows fasteners 29, 29' to be left in heart 5 following coronary bypass surgery without need for removal. Sutures 30, 30' attached to the fasteners 29, 29' may also be bioabsorbable, such that following use, sutures 30, 30' may be cut close to the respective fasteners 29, 29' and the remaining short end left behind. Although only two fasteners 29, 29' are shown, more or fewer fasteners can be used depending on the surgical requirements.

The outer diameter of helix-shaped fasteners 29, 29' may need to be somewhat larger than four millimeters and it is anticipated that the ideal diameter ranges between five millimeters and eight millimeters, as determined through empirical observations.

Moreover, sutures 30, 30' may be attached to a frame outside the surface of the skin, wherein the frame may encircle the limited thoracotomy or sternotomy used for cardiac access. Sutures 30, 30' may be attached to a frame which is also itself attached to the operating table. Preferably, helix-shaped fastener 29, 29' includes a beveled tip 31 so that it can easily drive into myocardium 6. Of course, the number of coils, dimensions, length, and pitch of helix-shaped fasteners 29, 29' can be varied in accordance with design requirements.

The mechanical insertion device used to deliver helix-shape fasteners 29, 29' can be of the type known commercially as the ORIGIN TACKER™, manufactured by Origin Medsystems, Inc., Menlo Park, Calif. In particular, this spiral tacking device is essentially a hand operated, pistol grip feeder of the helix-shaped fasteners wherein the helix-shaped fasteners are ejected from the front end of a feeding tube in which the fasteners are contained. Use of such a device for fixation of mesh in laparoscopic hernia repair is described in an article entitled "A Novel Technique for Anterior Hernia Repair" by Harold S. Golstein, M.D. and was published by Origin Medsystems in 1996.

Figure 7:
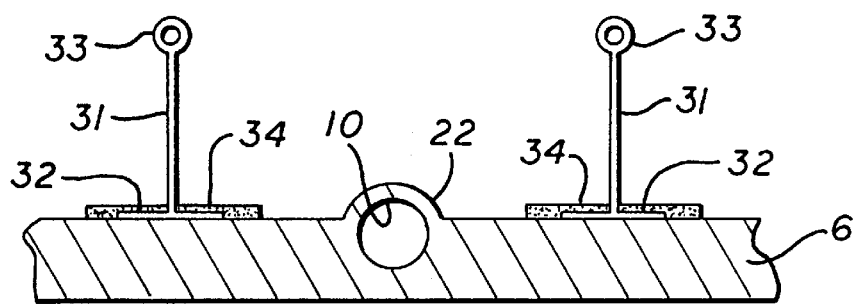
FIG. 7 is a side elevational view of an alternative embodiment of the present invention having control arms with feet directly bonded to the myocardium.

FIG. 7 is a side elevational view of an alternative embodiment of the present invention system comprising control arm 31 with outstretched feet 32 and attachment member 33 disposed on opposite ends. In this embodiment, feet 32 are embedded in a mound of adhesive 34. Thus, feet 32 are directly bonded to myocardium 6 without use of a pad as seen in the embodiment of FIG. 2. Again, adhesive 34, feet 32, and control arm 31 are made of bioabsorbable material so that at the conclusion of the operation, control arm 31 can be clipped off with only the lower stem and feet 32 left behind along with adhesive 34, all of which eventually dissolve.

A retractor can grasp the ring-like attachment member 33 to manipulate and control anastomotic site 22 via feet 32 and adhesive 34. Again, more or fewer of the present invention devices can be used at a specific anastomotic site.

Figure 8:
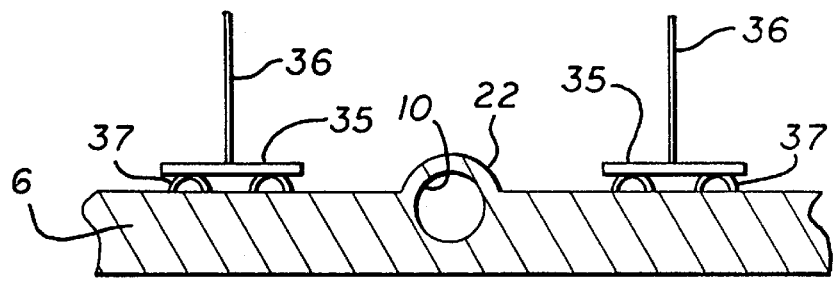
FIG. 8 is a side elevational view of an alternative embodiment of the present invention providing a pad with suction cups that adhere to the epicardium.

FIG. 8 is a side elevational view of an alternative embodiment of the present invention system having pad 35 with a suture 36 attached to the top surface of pad 35, while the bottom surface includes at least one miniature suction cup 37 which adheres in a conventional manner to myocardium 6. Alternatively, an adhesive can be added to strengthen the bond between suction cups 37 and myocardium 6. Suture 36 of course can be replaced with rigid or semirigid control arms as in some of the other embodiments. Any of the foregoing can be made from bioabsorbable materials.

Figure 9:
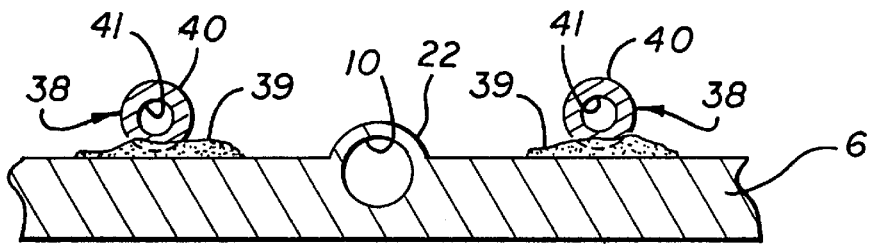
FIG. 9 is a side elevational view of an alternative embodiment of the present invention.
Figure 10:
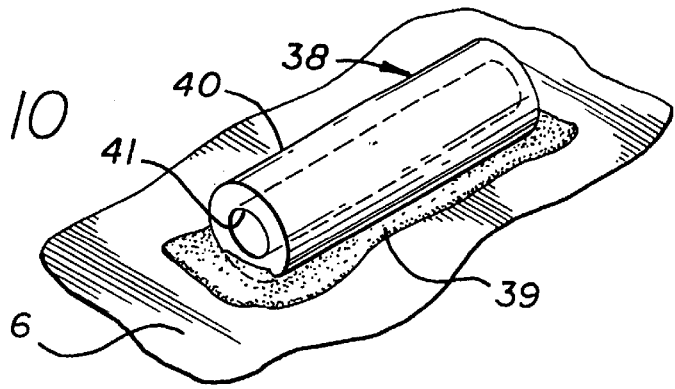
FIG. 10 is a perspective view of an alternative embodiment.

FIG. 9 is a side elevational view of an alternative embodiment of the present invention system providing short lengths of tubing 38 that are directly bonded to myocardium 6 using adhesive 39. Outer lip 40 of tubing 38 provides easy access and grasping by a surgical instrument such as a retractor to stabilize anastomotic site 22. Outer lip 40 also serves as an attachment member or platform so that other components can be attached or bonded thereto.

In yet another alternative embodiment, another more rigid section of tubing can be inserted inside hollow opening 41 of tubing 38 to serve as the control arm and for easier access by the retractor. Tubing 38 along with adhesive 39, if made from a bioabsorbable material, can be left behind after the surgical procedure.

Other modifications can be made to the present invention without departing from the scope thereof. The specific dimensions, shapes, and materials of construction are provided as examples, and substitutes are readily contemplated which do not depart from the invention.

What is claimed is:

1. A system for manipulating an internal organ during a surgical procedure comprising:
    a pad attached to an area of tissue of the internal organ;
    means for bonding the pad to the area of tissue; and
    a surgical instrument to grasp the pad to manipulate the area of tissue.

2. The system of claim 1, wherein the surgical instrument is a retractor.

3. The system of claim 1, wherein the pad is a biodegradable adhesive.

4. The system of claim 1, wherein the means for bonding the pad to the area of tissue includes a bioabsorbable adhesive.

5. The system of claim 1, wherein the means for bonding the pad to the area of tissue includes a collagen based bioabsorbable adhesive.

6. The system of claim 1, wherein the pad includes a material that is selected from the group of materials consisting of polyglycolic acid (PGA), poly-L-lactic acid (L-PLA), polyorthoesters, polyanhydrides, polyiminocarbonates, inorganic calcium phosphate, polyorthoesters, aliphatic polycarbonates, and polyphosphazenes.

7. The system of claim 3, wherein the adhesive pad is a bioabsorbable copolymer selected from the group of copolymers consisting of poly-L-lactic acid (L-PLA), polycaprolactone (PCL), collagen based adhesive, albumin based adhesive, and fibrin based adhesive.

8. The system of claim 1, wherein the pad is flexible and deforms to match an irregular surface of the area of tissue.

9. A system for locally stabilizing a beating heart during a surgical procedure, the system comprising:
    a pad for attaching to an area of cardiac tissue;
    means for controlling the pad to manipulate the area of cardiac tissue to create a locally stable area; and
    means for bonding the pad to the area of tissue.

10. The system of claim 9, wherein the means for controlling the pad is a control arm attached to the pad at a first end and having an attachment member at a second end, whereby the attachment member is manipulated during the surgical procedure to create a locally stable area at the area of cardiac tissue.

11. The system of claim 10, further comprising:
    a fluid adhesive applied to the heart and to the first end of the control arm and solidified therebetween; and
    additional fluid adhesive applied to the first end of the control arm and solidified thereupon.

12. The device of claim 10, wherein the control arm includes a tether.

13. The system of claim 10, wherein the control arm is semi-rigid.

14. The system of claim 9, wherein the means for bonding the pad to the area of tissue includes a bioabsorbable adhesive.

15. The system of claim 9, wherein the means for bonding the pad to the area of tissue includes a collagen based bioabsorbable adhesive.

16. The system of claim 10, wherein the first end of the control arm is encased in the pad.

17. The system of claim 10, wherein the pad and the control arm are made from a bioabsorbable material.

18. The system of claim 10, wherein the material for the control arm and pad is selected from the group of bioabsorbable materials consisting of polyglycolic acid (PGA), poly-L-lactic acid (L-PLA), polyorthoesters, polyanhydrides, polyiminocarbonates, inorganic calcium phosphate, polyorthoesters, aliphatic polycarbonates, and polyphosphazenes.

19. The system of claim 10, wherein the pad and the control arm include a copolymer selected from the group of copolymers consisting of poly-L-lactic acid (L-PLA), polycaprolactone (PCL), collagen based adhesive, albumin based adhesive, and fibrin based adhesive.

20. The system of claim 10, wherein the attachment member is a ring.

21. The system of claim 9, wherein the pad is removable.

22. The device of claim 9, wherein the pad is bioabsorbable and includes a plurality of attachment members for contacting an anastomotic site proximate to a vessel.

23. The device of claim 9, wherein the pad is bioabsorbable and is formed from a rigid material.

24. The device of claim 9, wherein the pad is bioabsorbable and has a contact surface for receiving a bioabsorbable adhesive to attach the pad to an anastomotic site.

25. The system of claim 9, wherein the pad is a bioabsorbable adhesive.

26. The system of claim 10, wherein the control arm is malleable.

27. The system of claim 10, wherein the control arm is rigid.

28. The system of claim 9, wherein the pad has a plurality of attachment members.

29. The system of claim 9, wherein the pad is flexible and deforms to match an irregular surface of the area of tissue.

30. A method of stabilizing a vessel during a surgical procedure, the method steps comprising:
    providing a pad having a control arm extending therefrom, wherein the control arm includes an attachment member;
    attaching the pad to an area of tissue; and
    grasping the attachment member to manipulate the control arm and the area of tissue.

31. The method according to claim 30, wherein the attachment member is grasped with a retractor.

32. The method according to claim 30, further comprising the step of removing the control arm.

33. The method according to claim 30, further comprising the steps of removing the pad and the control arm.

34. The method according to claim 30, wherein the pad and control arm are bioabsorbable, the method further comprising the steps of dissolving the pad and the control arm.

35. The method according to claim 30, wherein the step of attaching the pad to tissue includes the step of providing a bioabsorbable adhesive.

36. The method according to claim 30, wherein the step of attaching the pad to tissue utilizes a bioabsorbable mechanical fastener.

37. A system for manipulating an internal organ during a surgical procedure, the system comprising:

a pad for attaching to an area of tissue associated with the internal organ;

means for bonding the pad to the area of tissue; and means for controlling the pad and thereby manipulating the area of tissue to create a locally stable area.

38. The system of claim 37, wherein the means for controlling the pad is a control arm attached to the pad at a first end and having an attachment member at a second end, wherein the attachment member is manipulated to obtain a locally stable area at the area of tissue.

39. The system of claim 38, further comprising:

a fluid adhesive applied to the area of tissue and to the first end of the control arm and solidified therebetween; and additional fluid adhesive applied to the first end of the control arm and solidified thereupon.

40. The system of claim 38, wherein the control arm is semi-rigid.

41. The system of claim 38, wherein the control arm is rigid.

42. The system of claim 37, wherein the internal organ is the heart.

43. The system of claim 37, wherein the pad is a biodegradable adhesive.

44. The system of claim 37, wherein the means for bonding the pad to the area of tissue includes a bioabsorbable adhesive.

45. The system of claim 44, wherein the bioabsorbable adhesive is a copolymer selected from the group of copolymers consisting of poly-L-lactic acid (L-PLA), polycaprolactone (PCL), collagen based adhesive, albumin based adhesive, and fibrin based adhesive.

46. The system of claim 37, wherein the means for bonding the pad to the area of tissue includes a collagen based bioabsorbable adhesive.

47. The system of claim 37, wherein the first end of the control arm is encased in the pad.

48. The system of claim 37, wherein the pad and the control arm are made from a bioabsorbable material.

49. The system of claim 48, wherein the bioabsorbable material is selected from the group of materials consisting of polyglycolic acid (PGA), poly-L-lactic acid (LPLA), polyorthoesters, polyanhydrides, polyiminocarbonates, inorganic calcium phosphate, polyorthoesters, aliphatic polycarbonates, and polyphosphazenes.

50. The system of claim 37, wherein the pad is flexible and deforms to match an irregular surface of the area of tissue.

51. The system of claim 37, wherein the system includes a plurality of control arms wherein each control arm is attached to the pad at the first end and includes an attachment member at the second end.

52. The system of claim 37, wherein the pad includes a section of bioabsorbable tubing.

53. A system for locally stabilizing a beating heart during a surgical procedure, the system comprising:

a pad for attaching to an area of cardiac tissue; and means for controlling the pad to manipulate the area of cardiac tissue to create a locally stable area.

54. The system of claim 53, wherein the pad attachment means is biodegradable.

55. A system for manipulating an internal organ during a surgical procedure, the system comprising:

a pad for attaching to an area of tissue of the internal organ; and means for controlling the pad to manipulate an area of tissue.

56. The system of claim 55, wherein the internal organ is the heart.

57. The system of claim 56, wherein the pad further comprises a pad attachment means that is biodegradable.

* * * * *